US009341588B2

(12) United States Patent
Palazzotto et al.

(10) Patent No.: US 9,341,588 B2
(45) Date of Patent: May 17, 2016

(54) SENSOR ELEMENT, METHOD OF MAKING THE SAME, AND SENSOR DEVICE INCLUDING THE SAME

(75) Inventors: Michael C. Palazzotto, Woodbury, MN (US); Stefan H. Gryska, Woodbury, MN (US); Tzu-Chen Lee, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 401 days.

(21) Appl. No.: 13/825,663

(22) PCT Filed: Aug. 25, 2011

(86) PCT No.: PCT/US2011/049145
§ 371 (c)(1),
(2), (4) Date: Mar. 22, 2013

(87) PCT Pub. No.: WO2012/044419
PCT Pub. Date: Apr. 5, 2012

(65) Prior Publication Data
US 2013/0186177 A1 Jul. 25, 2013

Related U.S. Application Data

(60) Provisional application No. 61/388,130, filed on Sep. 30, 2010.

(51) Int. Cl.
*G01N 27/22* (2006.01)
*B82Y 15/00* (2011.01)

(52) U.S. Cl.
CPC .............. *G01N 27/226* (2013.01); *B82Y 15/00* (2013.01); *G01N 27/227* (2013.01); *Y10T 29/49117* (2015.01)

(58) Field of Classification Search
CPC ..... B82Y 15/00; G01N 27/226; G01N 27/227
See application file for complete search history.

(56) References Cited

U.S. PATENT DOCUMENTS

| 6,014,889 | A | * | 1/2000 | Castor ................ G01N 33/0011 250/343 |
| 7,449,146 | B2 | | 11/2008 | Rakow |

(Continued)

FOREIGN PATENT DOCUMENTS

| JP | 2003-227806 | 8/2003 |
| WO | WO 2005-012397 | 2/2005 |

(Continued)

OTHER PUBLICATIONS

Srivastava, A. K. "Detection of volatile organic compounds (VOCs) using SnO 2 gas-sensor array and artificial neural network." Sensors and Actuators B: Chemical 96.1 (2003): 24-37.*

(Continued)

*Primary Examiner* — Lisa Caputo
*Assistant Examiner* — Punam Roy
(74) *Attorney, Agent, or Firm* — Yufeng Dong

(57) ABSTRACT

A sensor element (100) includes a first conductive electrode (120) having a first conductive member (122) electrically coupled thereto; an absorptive dielectric layer (130) comprising a polymer of intrinsic microporosity; and a second conductive electrode (140) having a second conductive member (142) electrically coupled thereto. The second conductive electrode comprises carbon nanotubes and is permeable to at least one organic vapor. The absorptive dielectric layer is at least partially disposed between the first conductive electrode and the second conductive electrode. A method of making the sensor element, and sensor device (200) containing it, are also disclosed.

19 Claims, 1 Drawing Sheet

(56) References Cited

U.S. PATENT DOCUMENTS

| | | | |
|---|---|---|---|
| 7,556,774 | B2 | 7/2009 | Rakow |
| 7,767,143 | B2 | 8/2010 | Wendland |
| 8,378,694 | B2 | 2/2013 | David |
| 8,409,511 | B2 | 4/2013 | Thomas |
| 2004/0069046 | A1* | 4/2004 | Sunshine ............ G01N 33/0031 73/23.34 |
| 2005/0045493 | A1 | 3/2005 | Mahurin |
| 2005/0183492 | A1 | 8/2005 | Rao |
| 2006/0246273 | A1 | 11/2006 | McKeown |
| 2006/0249402 | A1 | 11/2006 | Snow |
| 2006/0267051 | A1* | 11/2006 | Gstrein ................ G01N 27/129 257/253 |
| 2007/0048180 | A1 | 3/2007 | Gabriel |
| 2007/0141580 | A1 | 6/2007 | David |
| 2007/0292957 | A1* | 12/2007 | Chua .................. G01N 15/0826 436/5 |
| 2008/0063575 | A1 | 3/2008 | Rakow |
| 2009/0091337 | A1 | 4/2009 | Robinson |
| 2010/0140600 | A1 | 6/2010 | Clough |
| 2010/0213954 | A1 | 8/2010 | Yao |
| 2010/0216273 | A1 | 8/2010 | Yao |
| 2010/0277740 | A1 | 11/2010 | Hulteen |
| 2011/0031983 | A1 | 2/2011 | David |
| 2011/0045601 | A1 | 2/2011 | Gryska |
| 2013/0088244 | A1 | 4/2013 | Gryska et al. |

FOREIGN PATENT DOCUMENTS

| | | |
|---|---|---|
| WO | WO 2005-033685 | 4/2005 |
| WO | WO 2006-099518 | 9/2006 |
| WO | 2008/079703 | 7/2008 |
| WO | WO 2009-002624 | 12/2008 |
| WO | WO 2009-045733 | 4/2009 |
| WO | WO 2009-046011 | 4/2009 |
| WO | WO 2010-075333 | 7/2010 |
| WO | WO 2011-159480 | 12/2011 |
| WO | WO 2012-050686 | 4/2012 |
| WO | WO 2012-141925 | 10/2012 |

OTHER PUBLICATIONS

Written Opinion of the International Searching Authority for PCT/US2011/049145. Mar. 31, 2013.*
Budd, "Polymers of Intrinsic Microporosity (PIMs): Robust, Solution-Processable, Organic Microporous Materials," Chem. Commun., 2004, pp. 230-231.
Budd, "Solution-Processed, Organophilic Membrane Derived from a Polymer of Intrinsic Microporosity", Advanced Materials, Mar. 2004, vol. 16, No. 5, pp. 456-459.
Jesen, "SiO2-Multiwalled Carbon Nanotube Base Gas Sensor", Advanced Materials Research, 2008, vols. 55-57, pp. 261-264.
Lee, "Applications of Singlewalled Carbon Nanotubes-polypyrrole nanocomposites to Supercapacitors and gas sensors", Polymer Preprints, 2005, vol. 46, No. 1, p. 186.
McKeown, "Polymers of Intrinsic Microporosity (PIMs): Bridging the Void between Microporous and Polymeric Materials," Chem. Eur. J., 2005, vol. 11, No. 9, pp. 2610-2620.
Snow, "Chemical vapor detection using single-walled carbon nanotubes", Chem. Soc. Rev., 2006, vol. 35, pp. 790-798.
Snow, "Chemical Detection with a Single-Walled Carbon Nanotube Capacitor", Science, Mar. 25, 2005, vol. 307, pp. 1942-1945.
Valcarcel, "Role of Carbon Nanotubes in Analytical Science", Anal. Chem., 2007, vol. 79, pp. 4788-4797.
International Search Report for PCT International Application No. PCT/US2011/049145, mailed on Nov. 24, 2011, 4 pages.
Palazzotto, Co-pending U.S. Appl. No. 13/825,660 entitled "Sensor Element, Method of Making the Same, and Sensor Device Including the Same", filed Sep. 7, 2011.

* cited by examiner

SENSOR ELEMENT, METHOD OF MAKING THE SAME, AND SENSOR DEVICE INCLUDING THE SAME

BACKGROUND

The ability to detect chemical vapors, especially volatile organic compounds (VOCs), is important in many applications including environmental monitoring and the like. Such detection and/or monitoring of organic vapors may find particular use in, for example, so called "end of service life indicators" which are desired for personal protective equipment such as respirators.

Many methods for the detection of chemical analytes have been developed including, for example, optical, gravimetric, and microelectromechanical (MEMS) methods. In particular, sensors that monitor electrical properties such as capacitance, impedance, resistance, etc., have been developed. Often, such sensors rely on the change that occurs in the electrical properties of a material upon adsorption of an analyte onto, or absorption of an analyte into, the material.

In one vapor sensor design, a layer of a polymer of intrinsic micoporosity (PIM) is sandwiched between vapor impermeable electrodes held at a voltage bias, forming a capacitor. PIMs pack poorly at the molecular level, and hence are readily permeable by organic small molecules. As organic vapors accumulate (e.g., by absorption and/or adsorption) in the PIM layer they accumulate in the pores, and the dielectric constant of the material between the electrodes increases causing a change in capacitance that can be measured. However, if the electrodes are impermeable to organic vapors then there can be limited exposed surface of the PIM layer through which vapor absorption can occur.

To overcome this problem, discontinuous electrodes having openings therethrough and interdigitated electrode configurations have been used. However, it remains desirable to have sensor elements suitable for use in sensor devices for rapidly detecting organic vapors with good sensitivity.

SUMMARY

In one aspect, the present disclosure provides a sensor element comprising:
first conductive electrode;
an absorptive dielectric layer comprising a polymer of intrinsic microporosity; and
a second conductive electrode,
wherein the second conductive electrode comprises carbon nanotubes and is permeable to at least one organic vapor, and wherein the absorptive dielectric layer is at least partially disposed between the first conductive electrode and the second conductive electrode.

In another aspect, the present disclosure provides method comprising steps of:
disposing an absorptive dielectric layer comprising a polymer of intrinsic microporosity on a first conductive electrode; and
disposing a second conductive electrode proximate at least a portion of the absorptive dielectric layer, wherein the second conductive electrode comprises carbon nanotubes and is permeable to at least one organic vapor, and wherein the absorptive dielectric layer is at least partially disposed between the first conductive electrode and the second conductive electrode.

The method may further comprise: disposing a first conductive member on the first conductive electrode; and disposing a second conductive member on the second conductive electrode.

Advantageously, sensor elements according to the present disclosure can differentiate between classes of chemical vapors, which is hitherto unknown for capacitive sensor elements of similar design, but using different porous conductive electrode materials.

Sensor elements according to the present disclosure are useful; for example, for making sensor devices.

Accordingly, in yet another aspect, the present disclosure provides a sensor device comprising:
a sensor chamber having an inlet opening,
a sensor element having a capacitance, disposed within the sensor chamber, and in fluid communication with the inlet opening, wherein the sensor element comprises:
first conductive electrode having a first conductive member electrically coupled thereto;
an absorptive dielectric layer comprising a polymer of intrinsic microporosity; and
a second conductive electrode having a second conductive member electrically coupled thereto, wherein the second conductive electrode comprises carbon nanotubes and is permeable to at least one organic vapor, and wherein the absorptive dielectric layer is at least partially disposed between the first conductive electrode and the second conductive electrode;
an operating circuit in electrical communication with the sensor element,
whereby if the sensor element is connected to a source of electrical power, the operating circuit measures the capacitance of the sensor element.

As used herein,
the term "organic compound" refers to a compound that comprises carbon and hydrogen atoms; and
the term "permeable" in reference to a layer of a material means that in areas wherein the layer is present, the layer is sufficiently porous to be non-reactively permeable through its thickness (e.g., at 25° C.) to at least one organic compound.

The foregoing aspects and embodiments may be implemented in any combination thereof, unless such combination is clearly erroneous in view of the teachings of the present disclosure. The features and advantages of the present disclosure will be further understood upon consideration of the detailed description as well as the appended claims.

It should be understood that numerous other modifications and embodiments can be devised by those skilled in the art, which fall within the scope and spirit of the principles of the disclosure. Figures may not be drawn to scale.

DETAILED DESCRIPTION

Figure 1:
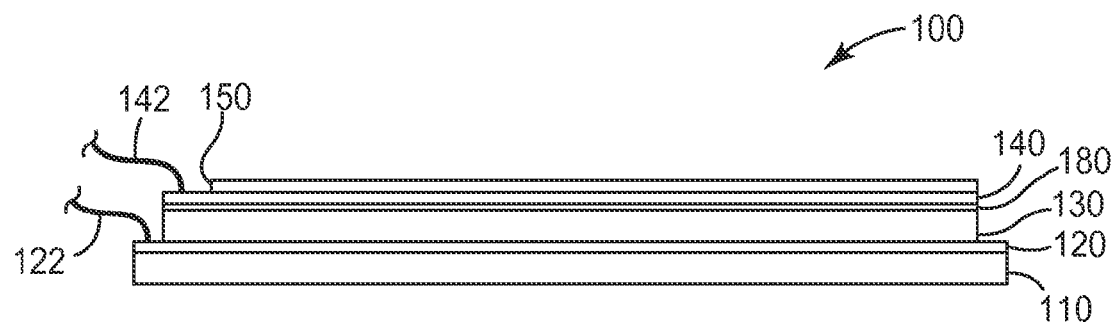
FIG. 1 is a schematic side view of an exemplary sensor element 100 according to the present disclosure.

Referring now to FIG. 1, sensor element 100 comprises dielectric 110 substrate supporting first conductive electrode 120 having an optional first conductive member 122 electrically coupled thereto. Absorptive dielectric layer 130 comprises a polymer of intrinsic microporosity, and is disposed between first conductive electrode 120 and second conductive electrode 140. Second conductive electrode 140 comprises carbon nanotubes and is permeable to at least one organic vapor. Optional ultrathin noble metal layer 180 is disposed between absorptive dielectric layer 130 and second conductive electrode 140. Optional second conductive member 142 is electrically coupled to second conductive electrode 140. Optional cover layer 150 is disposed on second conductive electrode 140. In the embodiment shown in FIG. 1, the first and second electrodes are generally planar, parallel, and disposed on opposite sides of the absorptive dielectric layer, although it will be recognized that other configurations are possible.

The sensor element is configured such that the absorptive dielectric layer is in sufficiently close proximity to the first conductive electrode and the second conductive electrode that the absorptive dielectric material contained in the layer will be capable of interacting with an electric field that is established by the electrodes. In operation of the sensor element, the absorptive dielectric layer exhibits a change in an electrical property upon absorption of one or more analytes (e.g., one or more organic vapors). In one embodiment, the electrical property is capacitance or a capacitance-related property as described below. Such a change in a capacitance-related property can be measured by imparting a charge differential between the first conductive electrode and the second conductive electrode (e.g., by imparting a voltage differential to the electrodes) and monitoring the property of the sensor element in response to the presence of the analyte. Such monitoring can be done by the use of an operating circuit, as described later herein.

The terms "capacitance" and "capacitance-related property" encompass any electrical property and the measurement thereof that is in general associated with the imparting of an electrical charge (whether static or time variant) and the monitoring of an electrical property during and/or after the imparting of the charge. Such properties include, for example, not only capacitance, but also impedance, inductance, admittance, current, resistance, and conductance, and may be measured according to various methods known in the art.

The absorptive dielectric layer (the term "layer" being used generically and encompassing any physical configuration) comprises at least in part an absorptive dielectric material. In this context, the term "absorptive dielectric material" means a material that is capable of absorbing an organic chemical analyte, and that can exhibit a measurable change in some electrical property of the material upon absorbing the organic analyte into the material.

While FIG. 1 depicts a parallel plate type of configuration, other configurations are also possible. For example, a configuration wherein the first and second electrodes are interdigitated is also possible and within the scope of the present disclosure.

In one embodiment, the absorptive dielectric material is chosen from the family of materials comprising so-called "polymers of intrinsic microporosity" (hereafter called PIMs). Such polymers include, but are not limited to, those disclosed in "Polymers of Intrinsic Microporosity (PIMs): Robust, Solution-Processable, Organic Microporous Materials," Budd et al., *Chem. Commun.*, 2004, pp. 230-231; in "Polymers of Intrinsic Microporosity (PIMs)," McKeown et al., *Chem. Eur. J.*, 2005, 11, No. 9, 2610-2620; in US Patent Application Publication 2006/0246273 to McKeown et al.; and in Published PCT application No. WO 2005/012397A2 to McKeown et al.

PIMs can be formulated via the use of any combination of monomers that member to a very rigid polymer within which there are sufficient structural features to induce a contorted structure. In various embodiments, PIMs can comprise organic macromolecules comprised of generally planar species connected by rigid linkers, said rigid linkers having a point of contortion such that two adjacent planar species connected by the rigid linkers are held in non-coplanar orientation. In further embodiments, such materials can comprise organic macromolecules comprised of first generally planar species connected by rigid linkers predominantly to a maximum of two other said first species, said rigid linkers having a point of contortion such that two adjacent first planar species connected by the rigid linkers are held in non-coplanar orientation. In various embodiments, such a point of contortion may comprise a spiro group, a bridged ring moiety or a sterically congested single covalent bond around which there is restricted rotation.

In a polymer with such a rigid and contorted structure, the polymer chains are unable to pack together efficiently, thus the polymer possesses intrinsic microporosity. Thus, PIMs have the advantage of possessing microporosity that is not significantly dependent on the thermal history of the material. PIMs thus may offer advantages in terms of being reproducibly manufacturable in large quantities, and in terms of not exhibiting properties that change upon aging, shelf life, etc.

In this context, the terms "microporous" and "microporosity" mean that the material has a significant amount of internal, interconnected pore volume, with the mean pore size (as characterized, for example, by sorption isotherm procedures) being less than about 100 nanometers (nm), typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed. Without being limited by theory or mechanism, applicant considers that the disclosed sensor element, relying on a microporous dielectric material, may have advantageous properties with regard to the sensor of an organic analyte, in that a measurable change in an electrical property of the dielectric material may be caused by the presence of the analyte molecules in the pores. Thus, it may be possible to detect the analyte without the analyte molecules being required to be solubilized in the polymeric material itself to a sufficient extent to cause a change in a property of the polymeric material such as swelling and/or expansion (although such a phenomenon may also occur and may also contribute to a measurable electrical response). Such a microporous nature of the absorptive dielectric material may contribute to increased sensitivity of the dielectric material to small amounts of organic analyte.

In various embodiments, the PIM comprises a porosity of at least about 10 percent, at least about 20 percent, or at least about 30 percent (as characterized, for example, by sorption isotherm techniques, such as those using instruments available under the trade designation AUTOSORB from Quantachrome Instruments of Boynton Beach, Fla.). Such porosity can provide good response to low levels of organic chemical analytes. However, the material should not have such a high pore volume that it is difficult to avoid electrical shorting or arcing between the first conductive electrode and the second conductive electrode. Thus, in various embodiments, the material comprises a porosity of at most about 90 percent, at most about 60 percent or at most about 40 percent.

Again without being limited by theory or mechanism, the size and distribution of the internal pores may be such that at least some of the organic analyte molecules in at least some of the pores may form a more highly condensed state (e.g., a quasi-liquid state) than they would otherwise be in (e.g., than they would be in the environment in which the analyte is monitored). This may result in analyte molecules collecting in the internal pores in larger numbers and/or at a higher concentration than they are present in the environment being monitored; in addition, or instead, the analyte molecules in this state may exhibit a higher dielectric constant (relative permittivity) than in an uncondensed vaporous or gaseous state. Thus, a sensor element based on a microporous absorptive dielectric material with appropriately chosen size and distribution of pores may exhibit superior sensitivity to small quantities of organic analyte. In various embodiments, the PIM comprises an average pore size of less about 50 nm, less than about 20 nm, or less than about 10 nm. In various embodiments, the PIM comprises an average pore size of greater than about 0.3 nm, greater than about 0.5 nm, or greater than about 1.0 nm.

In one embodiment, the PIM is a hydrophobic material (e.g., a hydrophobic organic polymeric material), that will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In one embodiment, the PIM comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, carbon nanotubes, etc.). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network as defined by applicant. However, if such a latex, sol-gel, etc., layer can be consolidated such that individual particles are no longer discernible, nor is it possible to discern areas of the assembly that were obtained from different particles, such a layer may then meet applicant's definition of a continuous matrix.

In certain embodiments, PIMs are soluble in common organic solvents and thus are amenable to conventional deposition processes such as coating.

In certain embodiments, after a PIM material is deposited (e.g., coated) or otherwise formed so as to comprise an absorptive dielectric layer, the material may be crosslinked using a suitable crosslinking agent, for example bis(benzonitrile)palladium(II) dichloride. This process may render the absorptive dielectric layer insoluble in organic solvents, and/or may enhance certain physical properties such as durability, abrasion resistance, etc., which may be desirable in certain applications.

In certain embodiments, the PIMs may be blended with other materials. For example, the PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

The absorptive dielectric material may have any thickness, but typically is in a range of from about 100 to 3000 nanometers (nm). More typically, the absorptive dielectric material forms a layer having a thickness in a range of from 300 nm to 1000 nm, or even from 400 to 800 nm.

The absorptive layer may contain additives such as fillers, antioxidants, light stabilizers in addition to the PIM material, but since they may tend to interfere with proper operation of the sensor element such additives are typically minimized or not present. Combinations of PIM materials may be used.

In various embodiments, an additional layer or layers of material that is not an absorptive dielectric material may be provided in proximity to the absorptive dielectric layer. Such a layer or layers may be provided for any of a variety of reasons; for example, as a protective layer or as a tie layer to improve adhesion.

In various embodiments, multiple individual layers of absorptive dielectric material can be used. For example, multiple layers of PIM materials can be used. Alternatively, one or more layers of some other absorptive dielectric material can be used in addition to a layer of PIM material. The various layers of absorptive dielectric material can be in direct contact with each other; or, they can be separated by a layer or layers present for some other purpose (e.g., passivation layers, tie layers, as described herein).

The first conductive electrode can comprise any suitable conductive material. Combinations of different materials (conductive and/or nonconductive) can be used, as different layers or as a mixture, as long as sufficient overall conductivity is provided, Typically, the first conductive electrode has a sheet resistance of less than about $10^7$ ohms/square. Examples of materials that can be used to make the first conductive electrode and/or second conductive electrode include, but are not limited to, organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, and combinations thereof.

The first conductive electrode can be of any thickness as long as it is conductive; for example, in a thickness in a range of from at least 4 nm to 400 nm, or from 10 nm to 200 nm. If the first conductive electrode is thicker than about 1000 nm or greater, it can become difficult for the second conductive electrode to bridge the edge of the electrode to make a conductive path. If the first conductive electrode is too thick, then the edge of the first conductive electrode may be sloped so that the second conductive electrode can make a continuous conductive path.

The second conductive electrode comprises carbon nanotubes. Useful carbon nanotubes include single-walled carbon nanotubes and multi-walled carbon nanotubes. In some embodiments, the second conductive electrode may have a carbon nanotubes content of at least 50, 60, 70, 80, 90, 95, 99, or even at least 99.9 percent by weight. In some embodiments, the second conductive electrode consists of, or consists essentially of, multi-walled carbon nanotubes. The second layer may include additional components as long as it remains permeable to at least one organic analyte. Combinations of different materials (conductive and/or nonconductive) can be used, as different layers or as a mixture, as long as sufficient overall conductivity and permeability is provided. Typically, the second conductive electrode has a sheet resistance of less than about $10^7$ ohms/square.

The second conductive electrode typically has a thickness in a range of from 0.1 to 100 micrometers, although other thicknesses may be used. For example, in some embodiments the second conductive electrode may have a thickness in a range of from 0.1 to 10 micrometers, or from 1 to 5 micrometers. Greater thicknesses may have undesirably low levels of permeability, while lesser thicknesses may become insufficiently conductive and/or difficult to electrically connect to the second conductive member. Since the second conductive electrode is permeable, the first electrode typically comprises a continuous, uninterrupted layer, but it may contain openings or other interruptions if desired.

The second conductive electrode can be prepared by any suitable technique such as, for example, solution/dispersion coating techniques (e.g., dip coating, spin coating, or flood coating). A surfactant may be used in conjunction with solutions/dispersions of the carbon nanotubes to enhance wetting of the absorptive layer. If the absorptive layer does not wet well with the carbon nanotubes solution/dispersion, then an ultra-thin (<1 nanometer thick) layer of a noble metal such as, for example, gold, platinum, or palladium, or a combination thereof, can be advantageously deposited on the absorptive layer prior to coating with the carbon nanotubes to facilitate wetting of the absorptive layer.

In an exemplary process for making such a sensor element, a dielectric substrate is provided (which may be a continuous slab, layer or film of material) that is in proximity to the first electrode and that may serve to provide physical strength and integrity to the finished sensor element. Any suitable material may be used, including glass, ceramic, plastic, etc. In large scale production, a polymeric film (such as polyester) may be used. In some embodiments, the dielectric substrate is an analyte-permeable material (e.g., silicone rubber or a microporous membrane).

In one embodiment, the first conductive electrode is provided on the dielectric substrate. The conductive layer may comprise any of the materials mentioned above, including blends or mixtures of conductive and nonconductive materials, and may be deposited by any suitable method, including but not limited to spin coating, dip coating, screen printing, transfer coating, sputter-coating, physical vapor deposition, chemical vapor deposition, or a combination of two or more of such methods. In an alternate embodiment, the conductive layer may be provided by placing a premade film (e.g., a metal foil or conductive tape) atop the dielectric substrate. This first conductive electrode may be provided as a continuous layer or as a discontinuous layer, as previously described.

In one embodiment, the first conductive electrode is provided such that the first conductive electrode is in proximity to, and/or in contact with, at least a portion of the dielectric substrate. In an alternative embodiment, an optional layer is present between at least a portion of the first conductive electrode, and the dielectric substrate. Such an optional layer may be used for any purpose (e.g., such as improving the bond between first conductive electrode and the dielectric substrate), as long as the layer does not interfere with the functioning of the sensor element.

The first and second conductive members may be electrically coupled to the first and second conductive electrodes at any appropriate point during assembly of the sensor element. For example, the first conductive member may be attached to the first conductive electrode immediately after deposition of the first conductive electrode and before deposition of the absorptive dielectric layer. In alternative embodiment, the absorptive dielectric layer may be deposited on the first conductive electrode such that an area of the first conductive electrode is left exposed for attachment to the first conductive member. Similarly, the second conductive member may be attached to the second conductive electrode immediately after deposition of the second conductive electrode and before deposition of the optional cover layer, or the optional cover layer may be deposited on the second conductive electrode such that an area of the second conductive electrode is left exposed for attachment to the second conductive member.

In one embodiment, the absorptive dielectric material is placed in proximity to the first conductive electrode by a coating process; for example, including but not limited to solvent coating, spin coating, dip coating, transfer coating, screen printing, and the like. In certain embodiments, the dielectric material is deposited in such a manner as to minimize the presence of defects, pinholes, etc., that might serve to compromise the performance of the sensor element. In a particular embodiment, the absorptive dielectric layer comprises a polymer of intrinsic microporosity that is deposited by coating a solution of PIM material upon a suitable dielectric substrate and allowing the solution to dry so as to form a solid layer comprising the PIM material.

An absorptive dielectric layer can also be provided by other methods. For example, a preformed film of absorptive dielectric material can be placed upon the second surface of the first conductive electrode. In an alternative embodiment, the absorptive dielectric material can be provided in particulate form (e.g., as a powder, as a suspension, or as a sol) and deposited in such a form onto a first conductive electrode so as to form a particulate coating. If desired, such a material can be consolidated so as to form a continuous matrix of absorptive dielectric material.

An optional protective cover or barrier layer can be provided in proximity to at least one of the first or second conductive electrodes. For example, in one embodiment, a cover layer can be placed atop the second conductive electrode, leaving an area of second conductive electrode accessible for electrical contact with the second conductive member electrical contact. Any such cover layer should not significantly interfere with the functioning of sensor element. For example, if the sensor element is configured such that an analyte of interest must pass through cover layer in order to reach the absorptive dielectric layer, the cover layer should be sufficiently permeable to the analyte.

The optional cover layer may be deposited by any method known in the art, including coating (e.g., spin coating, dip coating, solvent coating, vapor coating, transfer coating, screen printing, flexographic printing, and the like). In an alternate embodiment, the cover layer can comprise a premade layer (e.g., a film or tape) that is placed upon the second conductive electrode. In one embodiment, the cover layer is provided such that the cover layer is in direct contact with at least a portion of a major surface of the second conductive electrode. The cover layer may be the outermost layer of the sensor element, or may itself receive additional coatings or layers if desired.

In one embodiment, the first conductive electrode and the absorptive dielectric layer are in direct contact, with no interposing layer(s) therebetween. Likewise, in one embodiment, the second conductive electrode and the absorptive dielectric layer are in direct contact, with no interposing layer(s) therebetween. Such embodiments are pictured in FIG. 1. However, it is also contemplated that other, optional layers may be present between the first conductive electrode and the absorptive dielectric layer, and/or between the second conductive electrode and the absorptive dielectric layer. In such a case, either or both of the electrodes may not be in direct contact with some or all of a surface of the absorptive dielectric material. For example, a tie layer or layers may be used to improve the bonding between an electrode and the absorptive dielectric layer. Or, a passivation layer or layers (for example, a layer of silicon dioxide) may be placed in between a surface of the absorptive dielectric layer and an electrode surface, in order to minimize the possibility of arcing between the electrodes. In some embodiments, multiple such optional layers may be used; alternatively a single layer may serve multiple functions. Any such optional layer or layers such as the aforementioned tie layers, passivation layers, protective layers, cover layers, etc., may be used, for whatever purpose, as long as they do not significantly interfere with the desired functioning of the sensor element. For example, an optional layer should be sufficiently permeable to an analyte of interest if the sensor element is configured such that the analyte must pass through the optional layer in order to reach the absorptive dielectric layer.

In general, the edges of the first and/or second electrodes and/or absorptive dielectric layer can be aligned flush with each other, or, they may be recessed and/or extended relative to each other or any other layers that may be present.

In the deposition of the absorptive dielectric material onto the first conductive electrode, an electrically accessible area may be provided on the first conductive electrode to enable electrical contact between the electrode and an operating circuit. Similarly, if a cover layer is placed atop second conductive electrode, an electrically accessible area may be similarly provided. Such electrically accessible areas can be provided in any convenient location. In one embodiment, a connecting device (e.g., a contact pad, tab, or the like) may be placed in electrical contact with accessible area of first conductive electrode. Similarly, a connecting device may be placed likewise in contact with an accessible area of the second conductive electrode.

Upon absorption of sufficient analyte by the absorptive dielectric layer, a detectable change in an electrical property associated with the sensor element (including but not limited to, capacitance, impedance, admittance, current, or resistance) may occur. Such a detectable change may be detected by an operating circuit that is in electrical communication with the first and second conductive electrodes. In this context, "operating circuit" refers generally to an electrical apparatus that can be used to apply a voltage to the first conductive electrode and the second conductive electrode (thus imparting a charge differential to the electrodes), and/or to monitor an electrical property of the sensor element, wherein the electrical property may change in response to the presence of an organic analyte. In various embodiments, the operating circuit may monitor any or a combination of inductance, capacitance, voltage, resistance, conductance, current, impedance, phase angle, loss factor, or dissipation.

Such an operating circuit may comprise a single apparatus which both applies voltage to the electrodes, and monitors an electrical property. In an alternative embodiment, such an operating circuit may comprise two separate apparatuses, one to provide voltage, and one to monitor the signal. The operating circuit is typically electrically coupled to first conductive electrode and to second conductive electrode by conductive members.

Figure 2:
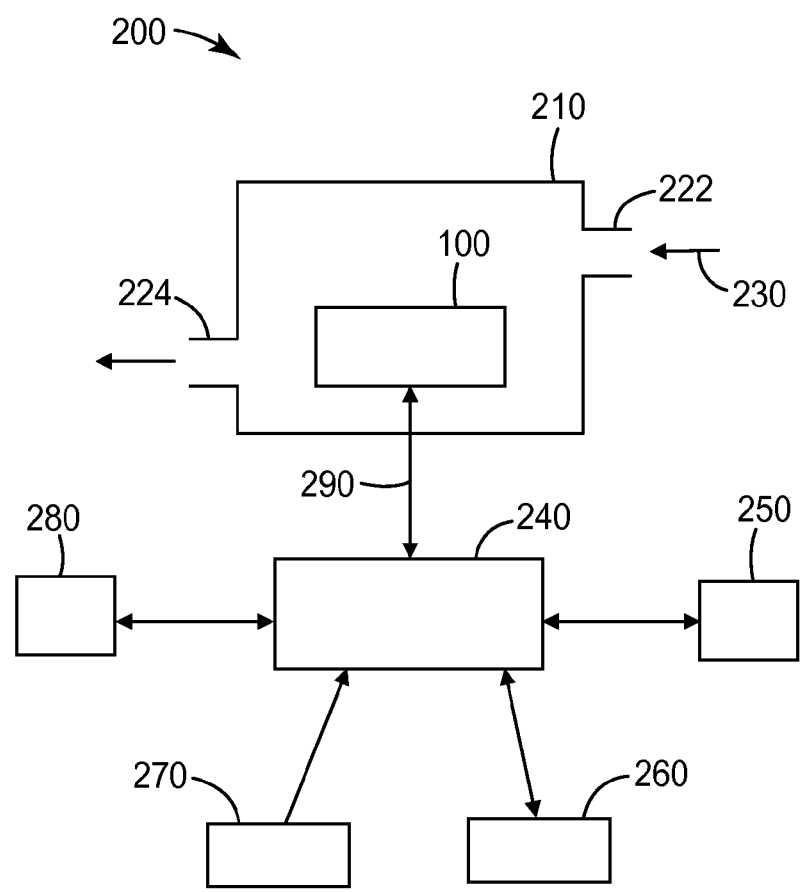
FIG. 2 is a schematic view of an exemplary sensor device 200 according to the present disclosure.

Referring now to FIG. 2, exemplary sensor device 200 includes a sensor chamber 210 having an inlet opening 222 and optional outlet opening 224. Sensor element 100 (as described hereinabove) is disposed within the sensor chamber 210, and is in fluid communication with the inlet opening 222 and optional outlet opening 224, if present. In typical operation, a sample containing analyte 230 enters sensing chamber 210, where it contacts sensor element 100. An operating circuit 240 is in electrical communication via conductive pathways 290 with sensor element 100. When connected to a source of electrical power 270, operating circuit 240 measures the capacitance of sensor element 100. In some embodiments, operating circuit 240 is communicatively coupled to data storage device 250, controller device 280, and/or display device 260.

In operation, the operating circuit 240 is in electrical communication with a source of electrical power 270.

Exemplary sources of electrical power include batteries, plug in power supplies, generators, hardwired power supplies, and RF generators (if the operating circuit includes an RF receiver).

The sensor chamber can be constructed of any solid material that is impermeable to the analyte. Examples include metal and/or plastic. Exemplary display devices 260 include LED displays, LCD displays, CRT displays, galvanic meters, and printers. Controller device 280, if present, includes hardware and/or software that directs operation of the operating circuit. Exemplary data storage devices 250 include flash memory cards, hard disks, digital tape, and CD R media.

In an alternative embodiment, the operating circuit may be provided in direct contact with the first and/or the second conductive electrode, either via connecting members, or by contacting some portion of the operating circuit directly to an electrically accessible area of each electrode. For example, an operating circuit can be provided that resides on a circuit board or a flexible circuit (either of which can also serve as the dielectric substrate). The first conductive electrode can then be deposited directly onto the dielectric substrate such that it is in direct contact with a portion of the operating circuit.

Sensor elements and sensor devices according to the present disclosure can be used to detect and/or monitor (whether qualitatively or quantitatively) the presence of an organic analyte or analytes. Such analytes can include, but are not limited to, hydrocarbons, fluorocarbons, alkanes, cycloalkanes, aromatic compounds, alcohols, ethers, esters, ketones, halocarbons, amines, organic acids, cyanates, nitrates, and nitriles, for example n-octane, cyclohexane, methyl ethyl ketone, acetone, ethyl acetate, carbon disulfide, carbon tetrachloride, benzene, styrene, toluene, xylenes, methyl chloroform, tetrahydrofuran, methanol, ethanol, isopropyl alcohol, n-butyl alcohol, t-butyl alcohol, 2-ethoxyethanol, acetic acid, 2-aminopyridine, ethylene glycol monomethyl ether, toluene-2,4-diisocyanate, nitromethane, and acetonitrile and the like. Organic analytes can be relatively nonpolar organic molecules or relatively polar organic molecules. Analytes are typically vapors; that is, molecules that are capable of condensing to form a solid or liquid under the ambient conditions of temperature and pressure that the analyte is experiencing (e.g., toluene, acetone, or heptane).

SELECT EMBODIMENTS OF THE DISCLOSURE

In a first embodiment, the present disclosure provides a sensor element comprising:

first conductive electrode;

an absorptive dielectric layer comprising a polymer of intrinsic microporosity; and a second conductive electrode, wherein the second conductive electrode comprises carbon nanotubes and is permeable to at least one organic vapor, and wherein the absorptive dielectric layer is at least partially disposed between the first conductive electrode and the second conductive electrode.

In a second embodiment, the present disclosure provides a sensor element according to the first embodiment, further comprising a dielectric substrate supporting the first conductive electrode.

In a third embodiment, the present disclosure provides a sensor element according to the second embodiment, wherein the dielectric substrate comprises a polymeric film.

In a fourth embodiment, the present disclosure provides a sensor element according to any one of the first to third embodiments, wherein the carbon nanotubes comprise at least 99 percent by weight of the second conductive electrode.

In a fifth embodiment, the present disclosure provides a sensor element according to any one of the first to fourth embodiments, wherein the carbon nanotubes comprise multi-walled carbon nanotubes.

In a sixth embodiment, the present disclosure provides a sensor element according to any one of the first to fifth embodiments, wherein the polymer of intrinsic microporosity comprises organic macromolecules comprised of generally planar species connected by rigid linkers, said rigid linkers having a point of contortion such that two adjacent planar species connected by one of the rigid linkers are held in non-coplanar orientation.

In a seventh embodiment, the present disclosure provides a sensor element according to any one of the first to sixth embodiments, wherein the first conductive electrode comprises carbon nanotubes and is permeable to at least one organic vapor.

In a eighth embodiment, the present disclosure provides a sensor element according to any one of the first to seventh embodiments, wherein the second conductive electrode is coextensive with a major surface of the absorptive dielectric layer.

In a ninth embodiment, the present disclosure provides a method comprising steps of:

disposing an absorptive dielectric layer comprising a polymer of intrinsic microporosity on a first conductive electrode; and disposing a second conductive electrode proximate at least a portion of the absorptive dielectric layer, wherein the second conductive electrode comprises carbon nanotubes and is permeable to at least one organic vapor, and wherein the absorptive dielectric layer is at least partially disposed between the first conductive electrode and the second conductive electrode.

In a tenth embodiment, the present disclosure provides a sensor element according to the ninth embodiment, wherein the first conductive electrode is supported on a dielectric substrate.

In an eleventh embodiment, the present disclosure provides a sensor element according to the tenth embodiment, wherein the dielectric substrate comprises a polymeric film.

In a twelfth embodiment, the present disclosure provides a sensor element according to any one of the ninth to eleventh embodiments, wherein the steps are sequential.

In a thirteenth embodiment, the present disclosure provides a sensor element according to any one of the ninth to twelfth embodiments, wherein the carbon nanotubes comprise at least 99 percent by weight of the second conductive electrode.

In a fourteenth embodiment, the present disclosure provides a sensor element according to any one of the ninth to thirteenth embodiments, wherein the carbon nanotubes comprise multi-walled carbon nanotubes.

In a fifteenth embodiment, the present disclosure provides a sensor element according to any one of the ninth to fourteenth embodiments, wherein the polymer of intrinsic microporosity comprises organic macromolecules comprised of generally planar species connected by rigid linkers, said rigid linkers having a point of contortion such that two adjacent planar species connected by the rigid linkers are held in non-coplanar orientation.

In a sixteenth embodiment, the present disclosure provides a sensor element according to any one of the ninth to fifteenth embodiments, wherein the first conductive electrode comprises carbon nanotubes and is permeable to at least one organic vapor.

In a seventeenth embodiment, the present disclosure provides a sensor element according to any one of the ninth to sixteenth embodiments, wherein the second conductive electrode is coextensive with a major surface of the absorptive dielectric layer.

In an eighteenth embodiment, the present disclosure provides a sensor device comprising:

a sensor chamber having an inlet opening, a sensor element having a capacitance, disposed within the sensor chamber, and in fluid communication with the inlet opening, wherein the sensor element comprises:

first conductive electrode having a first conductive member electrically coupled thereto;

an absorptive dielectric layer comprising a polymer of intrinsic microporosity; and a second conductive electrode having a second conductive member electrically coupled thereto, wherein the second conductive electrode comprises carbon nanotubes and is permeable to at least one organic vapor, and wherein the absorptive dielectric layer is at least partially disposed between the first conductive electrode and the second conductive electrode;

an operating circuit in electrical communication with the sensor element, whereby if the sensor element is connected to a source of electrical power, the operating circuit measures the capacitance of the sensor element.

In a nineteenth embodiment, the present disclosure provides a sensor device according to the eighteenth embodiment, wherein the sensor chamber further comprises an outlet opening in fluid communication with the inlet opening.

In a twentieth embodiment, the present disclosure provides a sensor device according to the eighteenth or nineteenth embodiment, further comprising a display device in communicatively coupled with the operating circuit.

In a twenty-first embodiment, the present disclosure provides a sensor device according to any one of the eighteenth to twentieth embodiments, wherein the carbon nanotubes comprise multi-walled carbon nanotubes.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

As used hereinbelow, the titanium bottom electrode corresponds to a first conductive electrode, and the top MWCNT electrode is equivalent to a second conductive electrode.

MATERIALS 1,1,1-Trichlorethane: anhydrous 1,1,1-trichlorethane with 99.5% purity obtained from Sigma-Aldrich Chemical Company of Milwaukee, Wis., catalog number 29899-9.
Acetone: acetone obtained as OMNISOLV ACETONE from EMD Chemicals Inc of Gibbstown, N.J., stock number AX0116-6.
Alconox Liqui-Nox: detergent obtained as ALCONOX LIQUI-NOX from Alconox, Inc. of White Plains, N.Y.
Chlorobenzene: spectrophotometric grade chlorobenzene with 99.9% purity, obtained from AlfaAesar of Ward Hill, Mass., stock number 22921.
Chloroform: obtained from EMD Chemicals Inc., stock number CX1055-6.
Ethyl Acetate: ethyl acetate obtained as OMNISOLV ETHYL ACETATE from EMD Chemicals Inc., stock number EX0241-6.
Gold: gold obtained as metal spatters, 99.999% typical purity from Cerac Inc. of Milwaukee, Wis.
Hexanes: hexanes obtained from EMD Chemicals Inc., stock number HX0299-6.
Isopropanol: isopropyl alcohol obtained from EMD Chemicals Inc., stock number PX1835-6.
MEK: methyl ethyl ketone obtained from J. T. Baker of Phillipsburg, N.J., stock number 9319-01.
MWCNT: multi-walled carbon nanotubes having outside diameters of 8-15 nanometers and lengths of about 10-50 micrometers obtained from Cheap Tubes Inc. of Brattleboro, Vt.
Schott glass: D263 thin glass with a thickness of 1.1 mm, length of 440 mm, and width of 440 mm, obtained from Schott North America of Elmsford, N.Y.
Removable Tape: pressure-sensitive adhesive tape obtained as SCOTCH BRAND REMOVABLE TAPE 811 from 3M Company of St. Paul, Minn.
Titanium: obtained as titanium slug, 9.5 mm×9.5 mm, 99.9+% purity from Alfa Aesar of Ward Hill, Mass.
Toluene: obtained from EMD Chemicals Inc.
Triton X-100: octylphenoxypolyethoxyethanol surfactant obtained as TRITON X-100 from Dow Chemical Co. of Midland, Mich.
Preparation of PIM PIM (Polymer of Intrinsic Microporosity) material was prepared from the monomers 5,5',6,6'-tetrahydroxy-3,3,3',3'-tetramethyl-1,1'-spirobisindane and tetrafluoroterephthalonitrile generally according to the procedure reported by Budd et al. in *Advanced Materials,* 2004, Vol. 16, No. 5, pp. 456-459. 19.31 grams of 5,5',6,6'-tetrahydroxy-3,3,3',3'-tetramethyl-1,1'-spirobisindane were combined with 11.34 g of tetrafluoroterephthalonitrile, 47.02 g potassium carbonate, and 500 milliliters of N,N-dimethylformamide, and the mixture was reacted at 65° C. for 48 hours. The resulting polymer was dissolved in tetrahydrofuran, precipitated three times from methanol, and then dried under vacuum at room temperature. A yellow solid product was obtained having a weight-average molecular weight of approximately 95,000 g/mole and a number-average molecular weight of approximately 64,300 g/mole, as determined by gel permeation chromatography analysis using light scattering detection.

Example 1

Schott glass was cut into 5.1-cm (2-inch) squares using a standard glass cutting tool. The Schott glass was prepared for vapor coating by sonicating it for 30 minutes at 50° C. using a Branson Model 1510 sonicator (from Branson Ultrasonics Corporation of Danbury, Conn.) with Alconox Liqui-Nox detergent, rinsing it well with hot tap water then deionized water (DI water), allowing it to drain, then oven drying it for 30 minutes at 65° C. This produced glass that was visually clean.

The glass substrate was masked with a thin strip approximately 2 mm wide of removable tape to isolate upper and lower electrode regions. This strip was placed roughly 1.8 cm from the bottom edge. A titanium bottom electrode was prepared by vapor depositing 100.0 nanometers of titanium onto the glass substrate at a rate of 0.5 nm/sec. A small margin around the border of the glass was blocked by the sample holder from the titanium coating. The removable tape was removed after vapor deposition. This produced an electrode having two regions covered with titanium: an upper region that was about 3 cm×5 cm and a lower region that was about 1.8 cm×5 cm. The small margin around the glass was not covered with titanium and there was a gap of about 2 mm between the two electrode regions which was protected from the titanium vapor deposition by the Removable Tape.

A 4.5 percent by weight solution of PIMS was prepared in chlorobenzene by mixing the components in a small jar and placing it on a roller mill (MINI BOTTLE ROLLER, number 348920, from Wheaton Science Products of Millville, N.J.) overnight to complete dissolution. The solution was filtered through a one-micrometer filter (ACRODISC 25 MM SYRINGE FILTER WITH 1 MICRON GLASS FIBER MEMBRANE from PALL Life Sciences of Ann Arbor, Mich.) prior to spin coating. The spin coating conditions were: one minute at 1200 rpm using a Model WS 400B-8NPP/LITE spin coater from Laurell Technologies Corporation of North Wales, Pa. Before spin coating, the lower portion of the electrode was masked with the Removable Tape to prevent it from being overcoated with PIMS. The titanium substrate was placed in the spin coater and about one ml of chlorobenzene was applied to clean off the surface. Then approximately 0.5 ml of the PIMS/chlorobenzene solution was applied. After completion of the coating process, the thickness was measured using a Model XP-1 Profilometer from AMBiOS Technology of Santa Cruz, Calif. The parameters used in the thickness measurement were a scan speed of 0.1 mm/sec, a scan length of 5 mm, a range of 10 microns, a stylus force of 0.20 mg and a filter level of 4. The thickness of the coating was between 500 and 600 nm on average. The sample was then placed in an oven at 100° C. for one hour to complete the drying process. The resulting sample had PIMS coated over approximately the top 3 cm of the substrate with the vapor deposited titanium exposed on the bottom 1.8 cm of the substrate.

Before applying the Multiwalled Carbon Nanotubes (MWCNTs) to the surface of the sample, a very thin layer of Gold, 0.7 nm, was deposited by thermal evaporation with a deposition rate of about 0.05 nm/sec to increase the wetting characteristics of the PIMS surface.

MWCNTs were purified as follows: They were first refluxed by 3 M $HNO_3$ for 4 hours, rinsed by DI water, filtered by a paper filter (WHATMAN FILTER PAPER GRADE 1 available from Whatman Inc. of Piscataway, N.J.), then dried at 80° C. to reduce metal catalysts. The dried MWCNTs were then put through an air burning process (480° C. furnace for 30 minutes) to remove amorphous carbons. The remaining material was then put through the $HNO_3$ reflux process (reflux by 3 M $HNO_3$ followed by rinsing with DI water, filtration and drying at 80° C.) again for one hour. Purified MWCNTs were added to a one percent by weight solution of Triton X-100 in DI water solution via ultrasonic agitation (using Ultrasonic Cleaner Model 3510 from Branson Ultrasonics Corporation, Danbury, Conn.) followed by centrifugal separation (using MODEL IEC CENTRA CL2 from Thermo Fisher Scientific Inc. of Waltham, Mass.) and decantation resulting in a stable one percent by weight dispersion of MWCNTs.

The dispersion of the MWCNTs was applied to the PIMS coated surface by knife coating (using a GARDCO MICROM II KNIFE COATER, available from the Paul N. Gardner Company, Inc. of Pompano Beach, Fla.). The knife coater setting was adjusted with the two micrometer dials on the ends of the knife coater. The micrometers were zeroed after placing the knife coater on a flat surface with the knife blade just touching the surface. The knife coater setting was then fixed by adjusting the micrometers to a setting of 6.5 on the smallest scale of the micrometers. This gave a gap between the knife blade and the substrate of about 0.16 mm.

The sample was baked at 125° C. in a $N_2$ environment for 13 minutes, followed by DI water rinsing to remove surfactant that was used in forming the MWCNT electrode. The coating was rebaked for over 10 minutes to complete the drying of the coating. The resistance of the MWCNT coating was about 6-8 kΩ from edge to edge of the MWCNT coating (~5 cm) after DI water rinsing and drying.

For capacitance testing, portions of the top MWCNT layer were removed to leave an approximately 14 mm×14 mm active sensor area over part of the upper region of the substrate (the approximately 3.0 cm×5 cm titanium coated region) with the MWCNT extending over the vapor deposited titanium covering the lower region of the substrate (the approximately 1.8 cm×5 cm titanium coated region). The top electrode of the sensor was the MWCNT layer which was in direct electrical contact with the approximately 1.8 cm×5 cm titanium coated region of the substrate. The bottom electrode of the sensor was the approximately 3.0 cm×5 cm titanium coated region of the substrate. Capacitance measurements were made on an LCR meter (INSTEK MODEL LCR-821 HIGH PRECISION LCR METER from Good Will Instruments, Co., Ltd. of Taipei, Taiwan) applying one volt at 1000 Hz across the top and bottom electrodes. Contact to the bottom and top electrodes of the sensor were made by attaching alligator clips to exposed titanium along the side of the sensor.

Cotton swabs saturated with various organic solvents were used to expose the sensor to vapors as the swab was brought close to the sensor surface. After exposure, nitrogen was blown over the surface of the sensor to purge it of the vapor. In most cases, the reading returned to the starting value in a few minutes. For Trial F, the sensor was exposed to moisture by taking a deep breath and blowing on the sensor. The relative humidity of the breath was measured to be about 90 percent by blowing on a humidity sensor (an iTHX-M i SERVER MICROSERVER TEMPERATURE/HUMIDITY SENSOR with an iTHP-5-D89-AMB temperature/humidity probe available from Omega of Stamford, Conn.). The results of the tests are shown in Table 1 (below).

TABLE 1

| TRIAL | ORGANIC VAPOR | INITIAL READING, nanofarads | DIRECTION OF CHANGE | MAGNITUDE OF CHANGE, nanofarads |
|---|---|---|---|---|
| A | acetone | 15 | increase | 2 to 3 |
| B | MEK | 15 | increase | 2 to 3 |
| C | hexanes | 15 | decrease | 0.5 to 1.0 |
| D | toluene | 15 | decrease | 0.5 to 1.0 |
| E | isopropanol | 15 | increase | 1 to 2 |
| F | breath (moisture) | 15 | increase | 2 to 3 |
| G | ethyl acetate | 14.2 | increase | 1 to 2 |
| H | chloroform | 14.4 | not determinable | <0.1 |
| I | 1,1,1-trichloroethane | 14.3 | decrease | 0.1 |

All examples given herein are to be considered non-limiting unless otherwise indicated. Various modifications and alterations of this disclosure may be made by those skilled in the art without departing from the scope and spirit of this disclosure, and it should be understood that this disclosure is not to be unduly limited to the illustrative embodiments set forth herein.

What is claimed is:

1. A sensor element comprising:
   first conductive electrode;
   an absorptive dielectric layer comprising a polymer of intrinsic microporosity; and
   a second conductive electrode,
   wherein the second conductive electrode comprises carbon nanotubes and is permeable to at least one organic vapor, and wherein the absorptive dielectric layer is at least partially disposed between the first conductive electrode and the second conductive electrode,
   wherein the carbon nanotubes comprise at least 99 percent by weight of the second conductive electrode, and
   wherein a change in an electrical property of the dielectric layer is measured by imparting a charge differential between the first conductive electrode and the second conductive electrode.

2. The sensor element of claim 1, further comprising a dielectric substrate supporting the first conductive electrode.

3. The sensor element of claim 2, wherein the dielectric substrate comprises a polymeric film.

4. The sensor element of claim 1, wherein the carbon nanotubes comprise multiwalled carbon nanotubes.

5. The sensor element of claim 1, wherein the polymer of intrinsic microporosity comprises organic macromolecules comprised of generally planar species connected by rigid linkers, said rigid linkers having a point of contortion such that two adjacent planar species connected by one of the rigid linkers are held in non-coplanar orientation.

6. The sensor element of claim 1, wherein the first conductive electrode comprises carbon nanotubes and is permeable to at least one organic vapor.

7. The sensor element of claim 1, wherein the second conductive electrode is coextensive with a major surface of the absorptive dielectric layer.

8. A method comprising steps of:
   disposing an absorptive dielectric layer comprising a polymer of intrinsic microporosity on a first conductive electrode; and
   disposing a second conductive electrode proximate at least a portion of the absorptive dielectric layer, wherein the second conductive electrode comprises carbon nanotubes and is permeable to at least one organic vapor, and wherein the absorptive dielectric layer is at least partially disposed between the first conductive electrode and the second conductive electrode, wherein the carbon nanotubes comprise at least 99 percent by weight of the second conductive electrode, and wherein a change in an electrical property of the dielectric layer is measured by imparting a charge differential between the first conductive electrode and the second conductive electrode.

9. The method of claim 8, wherein the first conductive electrode is supported on a dielectric substrate.

10. The method of claim 8, wherein the dielectric substrate comprises a polymeric film.

11. The method of claim 8, wherein the steps are sequential.

12. The method of claim 8, wherein the carbon nanotubes comprise multi-walled carbon nanotubes.

13. The method of claim 8, wherein the polymer of intrinsic microporosity comprises organic macromolecules comprised of generally planar species connected by rigid linkers, said rigid linkers having a point of contortion such that two adjacent planar species connected by the rigid linkers are held in non-coplanar orientation.

14. The method of claim 8, wherein the first conductive electrode comprises carbon nanotubes and is permeable to at least one organic vapor.

15. The method of claim 8, wherein the second conductive electrode is coextensive with a major surface of the absorptive dielectric layer.

16. A sensor device comprising:

a sensor chamber having an inlet opening, a sensor element having a capacitance, disposed within the sensor chamber, and in fluid communication with the inlet opening, wherein the sensor element comprises:

first conductive electrode having a first conductive member electrically coupled thereto;

an absorptive dielectric layer comprising a polymer of intrinsic microporosity; and a second conductive electrode having a second conductive member electrically coupled thereto, wherein the second conductive electrode comprises carbon nanotubes and is permeable to at least one organic vapor, wherein the absorptive dielectric layer is at least partially disposed between the first conductive electrode and the second conductive electrode, wherein the carbon nanotubes comprise at least 99 percent by weight of the second conductive electrode, and wherein a change in the capacitance of the sensor element is measured by imparting a charge differential between the first conductive electrode and the second conductive electrode;

an operating circuit in electrical communication with the sensor element, whereby if the sensor element is connected to a source of electrical power, the operating circuit measures the capacitance of the sensor element.

17. The sensor device of claim 16, wherein the sensor chamber further comprises an outlet opening in fluid communication with the inlet opening.

18. The sensor device of claim 16, further comprising a display device communicatively coupled with the operating circuit.

19. The sensor device of claim 16, wherein the carbon nanotubes comprise multiwalled carbon nanotubes.

* * * * *